(12) United States Patent
Wu et al.

(10) Patent No.: US 6,191,307 B1
(45) Date of Patent: Feb. 20, 2001

(54) PROCESS FOR MAKING BENZOIC ACIDS

(75) Inventors: Tse-Chong Wu; R. Carl Herndon, Jr., both of Baton Rouge, LA (US)

(73) Assignee: Albemarle Corporation, Richmond, VA (US)

( * ) Notice: Under 35 U.S.C. 154(b), the term of this patent shall be extended for 0 days.

(21) Appl. No.: 09/287,770

(22) Filed: Apr. 6, 1999

(51) Int. Cl.$^7$ .......................... C07C 51/38; C07C 63/04
(52) U.S. Cl. ............................................. 562/479; 562/493
(58) Field of Search ...................................... 562/493, 479

(56) References Cited

U.S. PATENT DOCUMENTS

| | | |
|---|---|---|
| 4,769,492 | 9/1988 | Kaieda et al. . |
| 4,769,493 | 9/1988 | Ito et al. . |
| 4,935,541 | 6/1990 | O'Reilly et al. . |
| 5,047,553 | 9/1991 | Nowak et al. . |
| 5,196,590 | 3/1993 | Oi et al. ................................ 562/493 |
| 5,233,085 | 8/1993 | O'Reilly et al. ...................... 562/479 |
| 5,523,476 | 6/1996 | Seki et al. . |
| 5,648,504 | 7/1997 | Seki et al. ............................. 549/246 |

OTHER PUBLICATIONS

Chen et al., "Preparation of 2,3,4,5–Tetrafluorobenzoic Acid" Chinese Journal of Pharmaceuticals, 1994, vol. 25, Issue 8, pp. 360–362 (5 pages translated).

Fertel, "Process Improvements in the Synthesis of 2,4, 5–Trifluorbenzoic Acid. Selective Hydrodefluorination of Tetrafluorophthalimides", Organic Process Research & Development, 1998, vol. 2, pp. 111–115.

O'Reilly, Neil J., et al., "An Expedient Route to the Quinolone Antibacterial Intermediate, 2,4,5–Trifluorobenzoic Acid", Syn. Lett., Oct. 1990, pp. 609–610.

Primary Examiner—Paul J. Killos
(74) Attorney, Agent, or Firm—Philip M. Pippenger

(57) ABSTRACT

A process of producing benzoic acids from phthalimides is described. The ability to dramatically reduce the reaction time in comparison to currently practiced processes by the addition of readily available compounds is demonstrated.

30 Claims, No Drawings

PROCESS FOR MAKING BENZOIC ACIDS

TECHNICAL FIELD

The subject of this invention is a process for making benzoic acids from phthalimides.

BACKGROUND

The production of benzoic acids from phthalimides by hydrolysis/decarboxylation is a reaction of considerable commercial importance. The conversion of tetrafluorophthalimide to 2,3,4,5-tetrafluorobenzoic acid, a precursor in the synthesis of Floxacin antibiotics, is an example of the reaction's commercial application. The hydrolysis/decarboxylation reaction can be particularly applicable in cases in which a phthalic acid or phthalic anhydride is converted to a phthalimide in order to protect the diacid or anhydride functionality from being compromised by a process which alters the substituency of the adjacent aromatic ring. Such hydrolysis/decarboxylation can subsequently be implemented to obtain a benzoic acid with the altered ring substituency.

The currently practiced method for hydrolysis/decarboxylation has a serious deficiency in that the reaction requires extremely long reaction times in order to come to substantial completion. Reaction times on the order of days are commonly encountered. Such long reaction times can cause the production of benzoic acids from phthalimides to be the rate limiting step in the synthesis of some organic compounds.

A method of conducting the hydrolysis/decarboxylation which reduces the reaction time presently required for the completion of the reaction would be a welcome contribution to the chemical and pharmaceutical industries.

SUMMARY OF THE INVENTION

It has been found that the addition of certain types of catalytic agents to the reaction has the effect of decreasing the reaction time of the hydrolysis/decarboxylation reaction as much as ten fold.

A catalytic agent, as the term is used herein, is an aprotic, dipolar compound which can solvate the phthalimide at reaction temperatures, and which is, additionally, soluble in water at reaction temperatures. Without desiring to be bound by theory, it is thought that the ability to enhance reaction rate lies in the improved solvation of the phthalimide in the aqueous media due to the presence of the catalytic agent. It has been noted that appropriate organic compounds which have relatively large permanent dipole moments give large decreases in reaction times.

Thus an embodiment of this invention is a process for making a benzoic acid which comprises heating a reaction mixture comprised of (1) a phthalimide, (2) an acid (3) water, and (4) an aprotic, dipolar, water-soluble catalytic agent, to thereby produce a benzoic acid at a rate greater than the rate at which the same benzoic acid would be produced under the same conditions, but in the absence of said catalytic agent. During the process, at least a portion of (1) is in solution in the reaction mixture.

In preferred embodiments, (1) is N-methyltetrafluorophthalimide, (2) is phosphoric acid, and (4) is sulfolane, diethyl ketone, or dimethyl sulfoxide.

Other acids can be used as well. In an additional preferred embodiment, (2) is sulfuric acid, and (4) is dimethyl sulfoxide.

The above and other embodiments will be apparent from the ensuing description and appended claims.

FURTHER DESCRIPTION OF THE INVENTION

Phthalimides which can be utilized in the process of this invention can be substituted or unsubstituted. The phthalimide aromatic ring as well as the imide nitrogen can bear substituents. Suitable substituents on the aromatic ring include, but are not limited to, alkyl, alkoxy, aryl, halogen atom, and others provided that they do not cause the phthalimide to be unable to undergo the hydrolysis/decarboxylation reaction. Suitable substituents on the imide nitrogen include alkyl, alkylhalo, alkoxy, amino, and others which, as in the case of phthalimide aromatic ring substituents, do not prevent the phthalimide from to undergoing hydrolysis/decarboxylation.

Examples of suitable phthalimides include, but are not limited to, 4-methoxymethylphthalimide, 3-chloro-5-cyanophthalimide, 3,6-difluorophthalimide, 4-octylphthalimide, 4-(2,2,3,3,4,4,5,5,6,6,7,7,7-tridecafluoroheptyl)phthalimide, 3,4,5-t-butyl-6-cyanophthalimide, 4-iodo-phthalimide, 3,6-diacetylphthalimide, 2,3-dihydro-1,3-dioxo-6[(2-propenylamino)carbonyl]-1H-isoindole-5-carboxylic acid, 3,5,6-trichlorophthalimide, 5,6-diiodophthalimide, 3-methylaminophthalimide, 4,5-dicyanophthalimide, 2,3-dihydro-1,3-dioxo-1H-Isoindoline-4-carboxylic acid, 4,5-bis(trifluoromethyl)-phthalimide, 3,4,5,6-tetrafluorophthalimide, N-methyl-3-chloro-5-cyanophthalimide, N-phenyl-3,4,5,6-tetrachlorophthalimide, N-methyl-3,6-dimethoxyphthalimide, N-[2-(diethylamino)ethyl]-3,4,5,6-tetrachlorophthalimide, N-methyl-4-bromophthalimide, N-methyl-3,4,5,6-tetra-chlorophthalimide, N-methyl-3,4,5,6-tetrafluorophthalimide, N-(p-bromophenyl)-4,6-dibromo-3-hydroxyphthalimide, N-4-pentynyl-3-chlorophthalimide, N-methyl-3,4,5-triaminophthalimide, N-hexadecyl-3,4,5,6-tetrabromophthalimide, and N-tetradecyl-3,4,5,6-tetraiodophthalimide. Preferable are halo-phthalimides such as 3,6-difluorophthalimide, 4-iodophthalimide, 5,6-diiodophthalimide, 3,4,5,6-tetrachlorophthalimide, N-phenyl-3,4,5,6-tetrachlorophthalimide, N-[2-(diethylamino)ethyl]-3,4,5,6-tetrachlorophthalimide, N-methyl-4-bromophthalimide, N-methyl-3,4,5,6-tetrachlorophthalimide, N-methyl-3,4,5,6-tetrafluorophthalimide, N-(p-bromophenyl)-4,6-dibromo-3-hy-droxyphthalimide, N-4-pentynyl-3-chlorophthalimide, N-hexadecyl-3,4,5,6-tetrabromophthalimide, and N-tetradecyl-3,4,5,6-tetraiodophthalimide. More preferable are N-aliphatic and N-aryl halophthalimides such as N-phenyl-3,4,5,6-tetrachlorophthalimide, N-methyl-4-bromophthalimide, N-methyl-3,4,5,6-tetrachlorophthalimide, N-methyl-3,4,5,6-tetrafluorophthalimide, N-4-pentynyl-3-chlorophthalimide, N-hexadecyl-3,4,5,6-tetrabromophthali-mide, N-tetradecyl-3,4,5,6-tetraiodophthalimide. Most preferable is N-methyl-3,4,5,6-tetrafluorophthalimide.

In conducting the process, an acid is utilized as a catalyst. Very strong organic acids such as trifluoroacetic acid may be used. However, mineral acids are preferable. Some examples of such are nitric acid, hydrochloric acid, sulfuric acid, phosphorous acid and phosphoric acid. Most preferable is phosphoric acid.

In the practice of this invention, it has been found that the catalytic agents which most efficaciously reduce the reaction time are those which are water-soluble yet retain the ability to solvate the phthalimide. To enable the practice of this invention, it is preferable to utilize a catalytic agent-phthalimide combination in which the catalytic agent has a water-solubility of at least about 5 grams of catalytic agent per 100 mL of water at 130° C., and the phthalimide has a solubility in the catalytic agent of at least about 0.1 gram of phthalimide per gram of catalytic agent at 130° C. Examples of such catalytic agent/phthalimide combinations are acetone/N-phenyl-3,4,5,6-tetrachlorophthalimide, diethyl sulfone/N-methyl-3,4,5,6-tetrafluorophthalimide, diethyl sulfone/N-phenyl-3,4,5,6-tetrafluorophthalimide, dimethyl sulfone/N-methyl-3,4,6-trifluorophthal-imide, sulfolane/N-methyl-3,4,6-trifluorophthalimide, sulfolane/N-phenyl-3,4,5,6-tetrafluorophthalimide, diethyl ketone/N-methyl-3,4,5,6-tetrachlorophthalimide, diethylketone/N-methyltetrafluorophthalimide, sulfolane/N-methyltetrafluorophthalimide, dimethyl sulfoxide/N-methyltetrafluorophthalimide. It is more preferable to utilize a catalytic agent-phthalimide combination in which the catalytic agent has a water-solubility of at least about 10 grams of catalytic agent per 100 mL of water at 130° C., and the phthalimide has a solubility in the catalytic agent of at least about 0.1 grams of phthalimide per gram of catalytic agent at 130° C. Examples of such are dimethyl sulfoxide/N-methyltetrachlorophthalimide, dimethyl sulfoxide/N-phenyltetrachlorophthalimide, sulfolane/N-phenyltetrachlorophthalimide, sulfolane/N-methyltetrachlorophthalimide. It is most preferable to utilize a catalytic agent-phthalimide combination, such as sulfolane/N-methyltetra-chlorophthalimide, in which the catalytic agent has a water-solubility of at least 20 grams of catalytic agent per 100 mL of water at 130° C., and the phthalimide has a solubility in the catalytic agent of at least about 0.5 grams of phthalimide per gram of catalytic agent at 130° C.

Without desiring to be bound by theory, it has been postulated that the above described solubility characteristics are related to the magnitude of the catalytic agent's permanent dipole as well as to its carbon atom content. Such carbon atoms can be arranged in chains which are linear or branched, as well as saturated or unsaturated. It is thus desirable that the compound or compounds which comprise the catalytic agent have a water-solubility of at least about 0.1 grams per mL of water at 130° C., a dipole moment strength of at least about 2 Debyes, and a carbon atom content in the range of about 2 carbon atoms to about 8 carbon atoms. Examples of such include sulfolane, dimethyl sulfoxide, dimethyl ketone, diethyl sulfoxide, diethyl sulfone, acetaldehyde, di-n-propyl sulfoxide, dipropyl sulfone, acetone, 2-butanone, dimethyl formamide, dimethyl acetamide, and the like. More desirable are catalytic agents having the above water-solubility and a dipole moment strength of at least about 3.2 Debyes and a carbon content in the range of from about 2 carbon atoms to about 4 carbon atoms, such as sulfolane, dimethyl sulfoxide, dimethyl sulfone, diethyl sulfoxide, diethyl sulfone, and similar solvents. Most desirable are catalytic agents with the above water-solubility, a dipole moment strength of about 4.8 Debyes and a carbon content of about 4 carbon atoms, such as sulfolane.

A feature of this invention is the coactive effect of the acid catalyst and the catalytic agent to give a substantial decrease in reaction time. In order to realize the benefits of this invention, it is preferable to use a mineral acid with an organic, dipolar compound containing up to about 8 carbon atoms in the molecule. Examples of acid catalyst/catalytic agent pairs which can facilitate the high yield formation of benzoic acids in less time than the acid catalyst alone are phosphoric acid/di n-propyl sulfoxide, phosphoric acid/dipropyl sulfone, hydrochloric acid/di n-propyl sulfoxide, hydrochloric acid/dipropyl sulfone, sulfuric acid/di n-propyl sulfoxide, hydrochloric acid/diethyl ketone, hydrochloric acid/sulfolane, hydrochloric acid/dimethyl sulfoxide, phosphoric acid/diethyl ketone, phosphoric acid/dimethyl sulfoxide, phosphoric acid/sulfolane and sulfuric acid/dimethyl sulfoxide. More preferable is the use of a mineral acid with a sulfone, sulfoxide or ketone containing up to about 4 carbon atoms in the molecule. Examples of such pairs are phosphoric acid/diethyl ketone, phosphoric acid/dimethyl sulfoxide, phosphoric acid/sulfolane and sulfuric acid/dimethyl sulfoxide. It is most preferable to use phosphoric acid/diethyl ketone, phosphoric acid/dimethyl sulfoxide, phosphoric acid/sulfolane or sulfuric acid/dimethyl sulfoxide.

However, not all acid catalyst/catalytic agent pairs are efficacious in giving a decreased reaction time with respect to the acid catalyst alone under otherwise similar or identical conditions. For example, it has been observed that the use of sulfuric acid with sulfolane can yield mostly impurities rather than the desired benzoic acid product. For this reason, if the efficacy of a particular acid catalyst/catalytic agent pair is not known, it is desirable to perform a simple test using the procedure of Example 3, hereinafter, to determine the magnitude of the coactive effect for that particular pair.

The presence of at least two equivalents of water in the reaction mixture is desirable in order for the benzoic acid formation reaction to go to substantial completion. In the absence of water, benzoic acids will not be formed.

The presence of at least two moles of water per mole of phthalimide is desirable in order for the substantial conversion of the phthalimide reactant to the corresponding benzoic acid. However, lesser amounts of water will enable the effectual operation of the process of this invention. The use of more than two moles of water per mole of phthalimide will not impair reaction product formation, and subject to practical limitations (e.g., reactor size, etc.) relatively large amounts of water can be employed.

Preferably, the weight ratio of phthalimide to catalytic agent is in the range of about 0.1 grams of phthalimide per gram of catalytic agent to about 10 grams of phthalimide per gram of catalytic agent. It is more preferable that the weight ratio of phthalimide to catalytic agent be in the range of about 0.5 grams of phthalimide per gram of catalytic agent to about 0.5 grams of phthalimide per gram of catalytic agent. It is most preferable that the weight ratio of phthalimide to catalytic agent be about 0.5 grams of phthalimide per gram of catalytic agent.

As the benzoic acid formation reaction is carried out, primary amines are formed in situ from the phthalimide. As the amines thus formed can neutralize the acid necessary for the reaction to proceed, it can be beneficial to carry out the process of this invention in the presence of an excess amount of acid with respect to the phthalimide. In the practice of this invention, it is desirable that the mole ratio of acid to phthalimide be in the range of about 1 mole of acid per mole of phthalimide to about 20 moles of acid per mole of phthalimide. It is more desirable that the mole ratio of acid to phthalimide be in the range of about 1.5 moles of acid per mole of phthalimide to about 10 moles of acid per mole of phthalimide. It is most desirable that the mole ratio of acid to phthalimide be about 2 moles of acid per mole of phthalimide.

It is preferable to have a weight ratio of water to catalytic agent in the range of about 0.5 gram of water per gram of catalytic agent to about 50 grams of water per gram of catalytic agent. It is more preferable to have a weight ratio of water to catalytic agent in the range of about 1 gram of water per gram of catalytic agent to about 10 grams of water per gram of catalytic agent. It is most preferable to have a weight ratio of water to catalytic agent of about 1 gram of water per gram of catalytic agent.

Another characteristic of this invention is the cooperative effect of the catalytic agent, the water, the acid and the phthalimide in achieving a decreased reaction time. Thus the amount of catalytic agent required relative to the amounts of water, acid and phthalimide to obtain a given decrease in reaction time can vary with the identity of the agent as well as the identity of the reactants undergoing hydrolysis/decarboxylation. It is therefore advisable to perform a simple test using the procedure of Example 3 to determine the magnitude of the effect of a particular concentration of catalytic agent.

Yet another feature of this invention is that it makes possible decreased reaction times without the use of extreme temperatures. It is desirable that the temperature be in the range of about 100° C. to about 200° C. A more desirable temperature range is from about 130° C. to about 170° C. It has been found that the temperature which gives the optimal rate increase can vary with the identities of the catalytic agent, the acid and the phthalimide. Thus, it can be possible to observe decreased reaction times with reactions occurring at temperatures outside the forementioned ranges. However, a temperature of 160° C. is most preferred.

Many variations in the method and order of reaction mixture component addition can be practiced which will enable realization of the benefits of this invention. The water can be introduced into the reaction mixture as a single component, or if desired, the water can be introduced into the reaction with one of the other components. The acid, the catalytic agent, the phthalimide or any combination of the three can be introduced in aqueous form. For example, as it can be desirable to introduce the acid as an aqueous solution, one method of adding water to the reaction mixture is to utilize an aqueous acid solution. The desired amount of water can be obtained by adjustment of the acid concentration of the aqueous mixture. In general, any mode and sequence of mixing the reaction components can be used.

The reaction mass comprised of phthalimide, acid catalyst, water and catalytic agent can form a single phase system or a multiphase system. For example, if the amount of a particular phthalimide in the reaction mass exceeds the capacity of the liquid phase of the reaction mass to completely dissolve the phthalimide, the reaction mass can form a two phase system consisting of unreacted phthalimide and the liquid phase of the reaction mass. In addition, the catalytic agent can have limited solubility in the water, acid and phthalimide mixture comprising the remainder of the reaction mass. In such a case, if enough catalytic agent is added to exceed the capacity of the remainder of the reaction mass to completely dissolve it, a two or three phase reaction mass is formed, depending on the presence or absence of a phthalimide phase. If the phthalimide and the catalytic agent completely dissolve in the remainder of the reaction mass, a one phase reaction mass results.

Heat can be supplied to the reaction in many ways. A mixture of the reaction components can be formed and subsequently heated. Alternatively, some of the reaction components can be mixed and heated, with the remaining components added to the preheated mixture at a later time. For example, an aqueous solution of the acid can be added to a preheated catalytic agent/phthalimide mixture. Another example is the addition of a preheated catalytic agent/acid solution to an aqueous phthalimide mixture. However, it is preferable to avoid heating the phthalimide with the water in the absence of the acid in order to avoid the increased formation of impurities.

As the reaction progresses, the pressure in a closed reaction vessel can reach a dangerously high level. Thus it can be desirable to vent the reaction vessel in order to reach or maintain a more desirable pressure. It is preferable to maintain the pressure under which the reaction is taking place in the range of about 0 psig to about 500 psig. It is more preferable to maintain a pressure in the range of about 50 psig to about 200 psig. Most desirable is a pressure of about 80 psig.

It is preferable to use mechanical agitation when conducting the process of this invention. A stirrer, rocking autoclave, shaker or other means of mixing or agitating can be used to cause the phthalimide, acid, water and catalytic agent to remain in intimate contact, thus facilitating the reaction.

After formation, the benzoic acids can be separated from the reaction mass by extraction, evaporation, or other separation methods. If separation by extraction is performed, toluene or other suitable solvents can be used.

The hydrolysis/decarboxylation reaction described above may yield amounts of other benzoic acids as well as the desired product. Specifically, if the phthalimide is not bilaterally symmetric (excluding the symmetry of the substituent on the imide nitrogen) two different benzoic acids can result. The use of a bilaterally symmetric phthalimide will result in the formation of only one type of benzoic acid.

Below are comparative illustrations of the production of tetrafluorobenzoic acid from N-methyl tetrafluorophthalimide both with and without a catalytic solution. Example 6 can serve to demonstrate the importance of selecting an aprotic compound as a catalytic agent.

EXAMPLE 1

Conversion of 3,4,5,6-Tetrafluorophthalimide (TFPI) to 2,3,4,5-Tetrafluorobenzoic acid (TFBA) in Water/Sulfolane Charge TFPI (10.0 g), $H_2O$ (16.0 g), $H_3PO_4$ (86%, 4.0 g), and sulfolane (20.0 g) to an autoclave (Hastelloy B, 100 mL). Set up in the hood and purge the autoclave with argon. Agitate at 160° C. for 9.5 hours. GC analysis showed 97% conversion and 67 GC area % TFBA.

EXAMPLE 2

Conversion of 3,4,5,6-Tetrafluorophthalimide to 2,3,4,5-Tetrafluorobenzoic acid in Water/Sulfolane Charge TFPI (6.5 g), $H_2O$ (22.0 g), $H_3PO_4$ (86%, 7.0 g), and sulfolane (10.0 g) to an autoclave (Hastelloy B, 100 mL). Set up in the hood and purge the autoclave with argon. Agitate at 160° C. for 10 hours. GC analysis showed 97% conversion and 72 GC area % TFBA. Quantitative GC analysis gave 74% yield.

EXAMPLE 3

Conversion of 3,4,5,6-Tetrafluorophthalimide to 2,3,4,5-Tetrafluorobenzoic acid in Water/Sulfolane Charge TFPI (14.0 g), $H_2O$ (14.0 g), $H_3PO_4$ (86%, 10.0 g), and sulfolane (20.0 g) to an autoclave (Hastelloy B, 100 mL). Set up in the hood and purge the autoclave with argon. Agitate at 160° C. for 11 hours. GC analysis showed 92% conversion and 86 GC area % TFBA. Quantitative GC analysis gave 78% yield.

EXAMPLE 4

Conversion of 3,4,5,6-Tetrafluorophthalimide to 2,3,4,5-Tetrafluorobenzoic acid in Water/Di-methyl Sulfoxide Charge TFPI (5.0 g), $H_2O$ (17.0 g), $H_3PO_4$ (86%, 3.0 g), and DMSO (20.0 g) to an autoclave (Hastelloy B, 100 mL). Set up in the hood and purge the autoclave with argon. Agitate at 140° C. for 10 hours. GC analysis showed 99% conversion and 55 GC area % TFBA.

EXAMPLE 5

Conversion of 3,4,5,6-Tetrafluorophthalimide to 2,3,4,5-Tetrafluorobenzoic acid in Water/Diethyl ketone Charge TFPI (5.0 g), $H_2O$ (37.7 g), $H_3PO_4$ (86%, 2.33 g), and DEK (10.0 g) to an autoclave (Hastelloy B, 100 mL). Set up in the hood and purge the autoclave with argon. Agitate at 160° C. for 12 hours. GC analysis showed 93% conversion and 74 GC area % TFBA.

EXAMPLE 6

Conversion of 3,4,5,6-Tetrafluorophthalimide to 2,3,4,5-Tetrafluorobenzoic acid in Water/Di-methyl sulfoxide Charge TFPI (5.0 g), $H_2O$ (17.0 g), $H_2PO_4$ (96%, 3.0 g), and DMSO (20.0 g) to an autoclave (Hastelloy B, 100 mL). Set up in the hood and purge the autoclave with argon. Agitate at 160° C. for 3 hours. GC analysis showed 96% conversion and 68 GC area % TFBA. Quantitative GC analysis gave 66% yield.

EXAMPLE 7

Conversion of 3,4,5,6-Tetrafluorophthalimide to 2,3,4,5-Tetrafluorobenzoic acid in Water/Sulfolane/ Diethyl ketone Charge TFPI (10.0 g), $H_2O$ (13.0 g), $H_3PO_4$ (86%, 7.0 g), DEK (5.0 g), and sulfolane (15.0 g) to an autoclave (Hastelloy B, 100 mL). Set up in the hood and purge the autoclave with argon. Agitate at 160° C. for 20.5 hours. GC analysis of an aliquot at 20.5 hours showed 99% conversion and 82 GC area % TFBA. GC analysis of an aliquot at 10 hours showed 93% conversion and 77 GC area % TFBA. Quantitative GC analysis showed 86% yield.

The following comparative example demonstrates the relatively long reaction time observed in the absence of a catalytic agent.

COMPARATIVE EXAMPLE 1

Conversion of 3,4,5,6-Tetrafluorophthalimide to 2,3,4,5-Tetrafluorobenzoic acid in Water Charge TFPI (10.0 g), $H_2O$ (33.1 g), and $H_3PO_4$ (86%, 4.40 g) to an autoclave (Hastelloy B, 100 mL). Set up in the hood and purge the autoclave with argon. Agitate at 160° C. for 30 hours. GC analysis of an aliquot at 30 hours showed 95% conversion and 77 GC area % TFBA. GC analysis of an aliquot at 10 hours showed 68% conversion and 52 GC area % TFBA.

In the following comparative example, the hydrolysis/decarboxylation takes place in the presence of a protic compound.

COMPARATIVE EXAMPLE 2

Conversion of 3,4,5,6-Tetrafluorophthalimide to 2,3,4,5-Tetrafluorobenzoic acid in Water/Acetic Acid Charge TFPI (10.0 g), $H_2O$ (17.0 g), $H_2SO_4$ (96%, 3.0 g), and $CH_3COOH$ (20.0 g) to an autoclave (Hastelloy B, 100 mL). Set up in the hood and purge the autoclave with argon. Agitate at 160° C. for 75 hours. GC analysis of an aliquot at 75 hours showed 90% conversion and 72 GC area % TFBA. GC analysis of an aliquot at 10 hours showed 25% conversion and 15 GC area % TFBA.

It is to be understood that the reactants and components referred to by chemical name or by formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient just as it existed at the time just before it was first contacted, blended or mixed with one or more other substances, components and/or ingredients in accordance with the present disclosure. Thus the fact that a substance, component or ingredient may have lost its original identity through a chemical reaction or transformation through the course of contacting, blending or mixing operations, if conducted in accordance with this disclosure and with the application of common sense and the ordinary skill of a chemist, is wholly immaterial for an accurate understanding and appreciation of the true meaning and substance of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process for making a benzoic acid which comprises heating a reaction mixture comprised of (1) a phthalimide, (2) a mineral acid, (3) water, and (4) an aprotic, dipolar, water-soluble catalytic agent in which (1) is soluble, and wherein at least a portion of (1) is in solution in said reaction mixture, such that a benzoic acid is produced at a rate greater than the rate at which said benzoic acid would be produced under the same conditions, but in the absence of said catalytic agent.

2. A process as in claim 1 wherein (1) is a halophthalimide.

3. A process as in claim 1 wherein (1) is a halophthalimide which is N-substituted with an alkyl or aryl substituent.

4. A process as in claim 1 wherein (1) is N-methyl tetrafluorophthalimide.

5. A process as in claim 1 wherein (2) is phosphoric acid.

6. A process as in claim 1 wherein (2) is sulfuric acid.

7. A process as in claim 1 or 5 wherein the dipole moment of the compound or compounds comprising the catalytic agent have a dipole moment strength of at least about 2 Debyes and a carbon content in the range of from about 2 carbon atoms to about 8 carbon atoms.

8. A process as in claim 1 or 5 wherein the dipole moment of the compound or compounds comprising the catalytic agent have a dipole moment strength in the range of at least about 2 Debyes and a carbon content in the range of from about 2 carbon atoms to about 4 carbon atoms.

9. A process as in claim 1 or 5 wherein the dipole moment of the compound or compounds comprising the catalytic agent have a dipole moment strength of at least about 3.2 Debyes and a carbon content in the range of from about 2 carbon atoms to about 8 carbon atoms.

10. A process as in claim 1 or 5 wherein the dipole moment of the compound or compounds comprising the catalytic agent have a dipole moment strength of at least about 3.2 Debyes and a carbon content in the range of from about 2 carbon atoms to about 4 carbon atoms.

11. A process as in claim 1 or 5 wherein the dipole moment of the compound or compounds comprising the catalytic agent have a dipole moment strength of about 4.8 Debyes and a carbon content of about 4 carbon atoms.

12. A process as in claim 1 wherein the temperature is in the range of about 100° C. to about 200° C.

13. A process as in claim 5 wherein the temperature is in the range of about 100° C. to about 200° C.

14. A process as in claim 6 wherein (1) is dimethyl sulfoxide and the temperature is about 160° C.

15. A process as in claim 1 wherein the weight ratio of (1) to (4) is in the range of about 0.1 gram of (1) per mole of (4) to about 10 grams of (1) per mole of (4).

16. A process as in claim 15 wherein the mole ratio of (2) to (1) is in the range of about 1 mole of (2) per mole of (1) to about 20 moles of (2) per mole of (1).

17. A process as in claim 16 wherein the weight ratio of (3) to (4) is in the range of from about 0.5 gram of (3) per gram of (4) to about 50 grams of (3) per gram of (4).

18. A process as in claim 1 wherein the weight ratio of (1) to (4) is about 0.5 gram of (1) per mole of (4).

19. A process as in claim 18 wherein the mole ratio of (2) to (1) is about 2 moles of (2) per mole of (1).

20. A process as in claim 19 wherein the weight ratio of (3) to (4) is about 1 gram of (3) per gram of (4).

21. A process as in claim 1 wherein (1) is a halophthalimide, wherein the solubility of (1) in (4) is at least about 0.1 gram of (1) per gram of (4) at 130° C. and the solubility of (4) in water is at least about 5 grams of (4) per 100 mL of water at 130° C., wherein the temperature is in the range of from about 100° C. to about 200° C., wherein the weight ratio of (1) to (4) is in the range of from about 0.1 gram of (1) per mole of (4) to about 10 grams of (1) per gram of (4), wherein the mole ratio of (2) to (1) is in the range of about 1 mole of (2) per mole of (1) to about 20 moles of (2) per mole of (1), wherein the weight ratio of (3) to (4) is in the range of from about 0.5 gram of (3) per gram of (4) to about 50 grams of (3) per gram of (4).

22. A process as in claim 1 wherein (1) is N-methyl tetrafluorophthalimide, (2) is phosphoric acid, (4) is sulfolane, dimethyl sulfoxide, or dimethyl ketone, wherein the weight ratio of (1) to (4) is in the range of about 0.5 gram of (1) per gram of (4) to about 5 grams of (1) per gram of (4), the mole ratio of (2) to (1) is in the range of about 1.5 moles of (2) per mole of (1) to about 10 moles of (2) per mole of (1), wherein the weight ratio of (3) to (4) is in the range of about 1 grams of (3) per gram of (4) to about 10 gram of (3) per gram of (4), and wherein the temperature is in the range of about 130° C. to about 170° C.

23. A process as in claim 1 wherein (1) is N-methyl tetrafluorophthalimide, (2) is sulfuric acid, (4) is dimethyl sulfoxide, wherein the weight ratio of (1) to (4) is about 0.25 gram of (1) per gram of (4), the mole ratio of (2) to (1) is about 1.4 moles of (2) per mole of (1), wherein the weight ratio of (3) to (4) is about 1 gram of (3) per gram of (4), and wherein the temperature is about 160° C.

24. A process as in claim 1 wherein (1) is N-methyl tetrafluorophthalimide, (2) is phosphoric acid, (4) is sulfolane, wherein the weight ratio of (1) to (4) is about 0.7 gram of (1) per gram of (4), the mole ratio of (2) to (1) is about 1.5 moles of (2) per mole of (1), wherein the weight ratio of (3) to (4) is about 1 gram of (3) per gram of (4), and wherein the temperature is about 160° C.

25. A process as in claim 1 wherein (1) is N-methyl tetrafluorophthalimide, (2) is phosphoric acid, (4) is dimethyl sulfoxide, wherein the weight ratio of (1) to (4) is about 0.25 gram of (1) per gram of (4), the mole ratio of (2) to (1) is about 1.4 moles of (2) per mole of (1), wherein the weight ratio of (3) to (4) is about 1 gram of (3) per gram of (4), and wherein the temperature is about 160° C.

26. A process as in claim 1 wherein (1) is N-methyl tetrafluorophthalimide, (2) is phosphoric acid, (4) is diethyl ketone, wherein the weight ratio of (1) to (4) is about 0.5 gram of (1) per gram of (4), the mole ratio of (2) to (1) is about 1 mole of (2) per mole of (1), wherein the weight ratio of (3) to (4) is about 4 grams of (3) per mole of (4), and wherein the temperature is about 160° C.

27. A process for making a benzoic acid which comprises heating a reaction mixture comprised of (1) a phthalimide, (2) an acid (3) water, and (4) a rate accelerating amount of an aprotic, dipolar, water soluble, catalytic agent in which (1) is soluble, at a temperature and for a time such that a benzoic acid is formed.

28. A process as in claim 27 wherein (1) is an N-substituted tetrafluorophthalimide, (2) is phosphoric acid, and (4) is an alkyl sulfoxide, an alkyl sulfone, or an alkyl ketone.

29. A process as in claim 27 wherein (1) is N-methyltetrafluorophthalimide, (2) is phosphoric acid, and (4) is dimethyl sulfoxide, sulfolane, or diethyl ketone.

30. A process as in claim 27 wherein (1) is an N-substituted tetrafluorophthalimide, (2) is sulfuric acid, and (4) is dimethyl sulfoxide.

* * * * *